US00PP20571P2

(12) United States Plant Patent
Wood

(10) Patent No.: US PP20,571 P2
(45) Date of Patent: Dec. 15, 2009

(54) ***HYDRANGEA* PLANT NAMED 'ABETWO'**

(50) Latin Name: *Hydrangea arborescens*
Varietal Denomination: Abetwo

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/229,591

(22) Filed: Aug. 25, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Susan B McCormick Ewoldt
(74) *Attorney, Agent, or Firm*—C. A. Whealy

(57) ABSTRACT

A new and distinct cultivar of *Hydrangea* plant named 'Abetwo', characterized by its upright and mounded plant habit; strong and sturdy stems; dark green-colored leaves; and large mophead-type inflorescences with numerous white-colored sterile flowers.

1 Drawing Sheet

Figure 1:
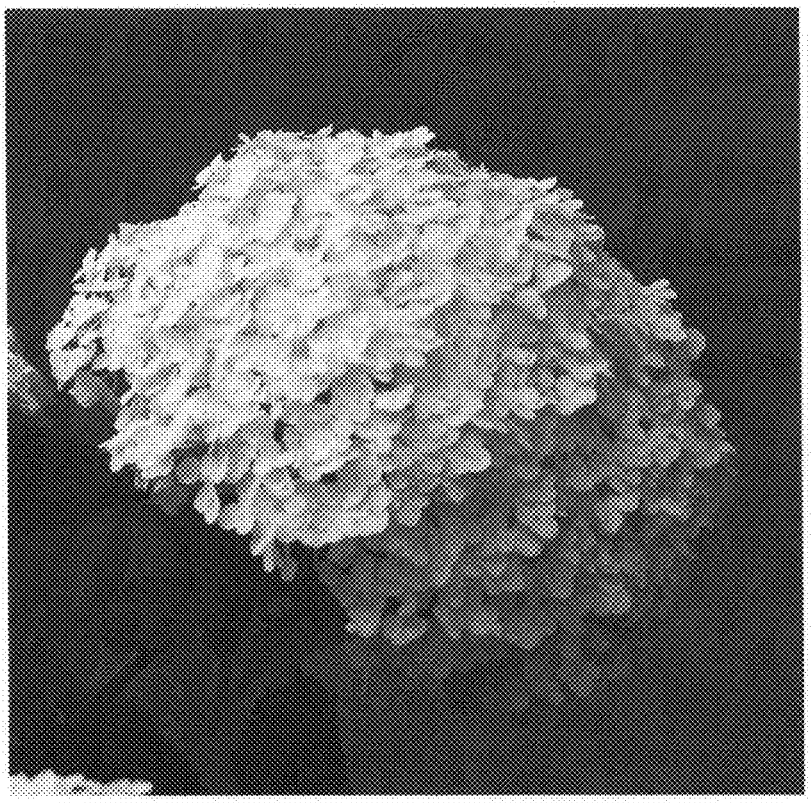

Botanical designation: *Hydrangea arborescens.*
Cultivar denomination: 'Abetwo'.

BACKGROUND OF THE INVENTION

The present invention relates to a new and distinct cultivar of *Hydrangea*, botanically known as *Hydrangea arborescens* and hereinafter referred to by the name 'Abetwo'.

The new *Hydrangea* is a product of a planned breeding program conducted by the Inventor in Grand Haven, Mich. The objective of the breeding program was to develop new *Hydrangeas* with strong stems and attractive foliage and flower coloration.

The new *Hydrangea* originated from an open-pollination in 2002 of the *Hydrangea* arborescens 'Annabelle', not patented, as the female, or seed parent and an unknown selection of *Hydrangea* arborescens. The new *Hydrangea* was discovered and selected by the Inventor in 2004 as a flowering plant within the progeny of the stated open-pollination in a controlled outdoor nursery environment in Grand Haven, Mich.

Asexual reproduction of the new cultivar by softwood cuttings in a controlled environment in Grand Haven, Mich. since 2004 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Abetwo'. These characteristics in combination distinguish 'Abetwo' as a new and distinct cultivar of *Hydrangea:*

1. Upright and mounded plant habit.
2. Strong and sturdy stems.
3. Dark green-colored leaves.
4. Large mophead-type inflorescences with numerous white-colored sterile flowers.

Plants of the new *Hydrangea* differ from plants of the female parent, 'Annabelle', in the following characteristics:

1. Plants of the new *Hydrangea* are taller than plants of 'Annabelle'.
2. Plants of the new *Hydrangea* have stronger and thicker stems than plants of 'Annabelle'.
3. Plants of the new *Hydrangea* have larger inflorescences than plants of 'Annabelle'.
4. Plants of the new *Hydrangea* have longer peduncles than plants of 'Annabelle'.
5. Plants of the new *Hydrangea* tolerate rain better than plants of 'Annabelle'.

Plants of the new *Hydrangea* can be compared to plants of *Hydrangea arborescens* 'White Dome', not patented. Plants of the new *Hydrangea* differ from plants of 'White Dome' in the following characteristics:

1. Plants of the new *Hydrangea* have mophead inflorescences whereas plants of 'White Dome' have lacecap inflorescences.
2. Plants of the new *Hydrangea* have showier inflorescences than plants of 'White Dome'.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

Figure 2:
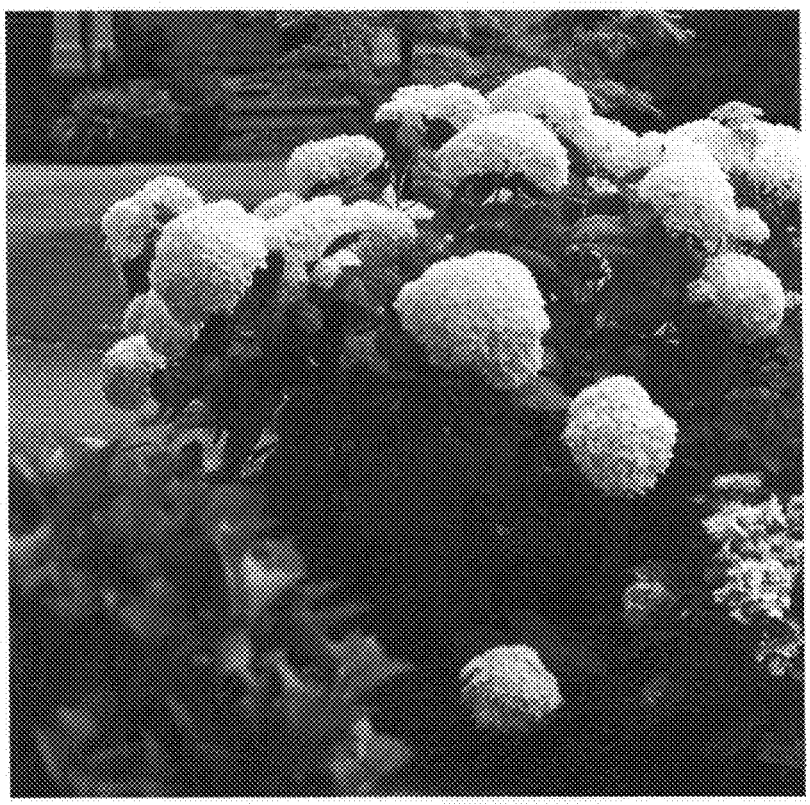

The photograph at the bottom of the sheet (FIG. 2) comprises a side perspective view of a typical flowering plant of 'Abetwo' grown in an outdoor nursery.

The photograph at the top of the sheet (FIG. 1) is a close-up view of a typical inflorescence of 'Abetwo'.

DETAILED BOTANICAL DESCRIPTION

Plants used for the aforementioned photographs and the following description were grown in Grand Haven, Mich. in ground beds in an outdoor nursery and under conditions which closely approximate commercial production conditions. Plants of the new *Hydrangea* had been growing for three years when the photographs and description were taken during the summer. In the following description, color references are made to The Royal Horticultural Society Colour Chart, 1995 Edition, except where general terms of ordinary dictionary significance are used.

Botanical description: *Hydrangea arborescens* 'Abetwo'.

Parentage:

*Female, or seed, parent.*—*Hydrangea arborescens* 'Annabelle', not patented.

*Male, or pollen, parent.*—Unknown selection of *Hydrangea arborescens,* not patented.

Propagation:

*Type cutting.*—By softwood cuttings.

*Time to initiate roots.*—About 20 days at temperatures of about 25° C.

*Time to produce a rooted young plant.*—About three months at temperatures of about 25° C.

*Root description.*—Fine, fibrous.

*Rooting habit.*—Freely branching; dense.

Plant description:

*Form/growth habit.*—Perennial shrub. Upright and mounded plant habit; broadly inverted triangle. Strong and sturdy lateral branches; vigorous growth habit.

*Plant height.*—About 1.25 meters.

*Plant diameter or area of spread.*—About 2 meters.

*Branching habit.*—Freely branching habit with about 36 lateral branches developing per plant.

*Lateral branches.*—Length: About 1 meter. Diameter: About 1 cm. Internode length: About 13 cm. Texture: Smooth, glabrous. Strength: Strong, sturdy. Color, young: Close to 144D. Color, mature: Close to 176D.

Foliage description:

*Arrangement.*—Opposite, simple.

*Length.*—About 20 cm.

*Width.*—About 15 cm.

*Shape.*—Ovate.

*Apex.*—Acuminate.

*Base.*—Obtuse to cuneate.

*Margin.*—Serrate.

*Texture, upper surface.*—Smooth, glabrous.

*Texture, lower surface.*—Pubescent.

*Venation pattern.*—Pinnate.

*Color.*—Developing and fully expanded leaves, upper surface: Close to 147A; venation, close to 147A. Developing and fully expanded leaves, lower surface: Close to 147B to 147C; venation, close to 147D.

*Petioles.*—Length: About 9.5 cm. Diameter: About 4 mm. Texture, upper and lower surfaces: Smooth, glabrous. Color, upper and lower surfaces: Close to 144D.

Flower description:

*Flower type and habit.*—Single sterile and fertile flowers arranged on terminal mophead-type panicles. Flowers face upright or outward.

*Fragrance.*—Slightly fragrant; pleasant.

*Natural flowering season.*—Continuous flowering throughout the summer in Grand Haven, Mich.

*Flower longevity, fertile flowers.*—Flowers last about three days on the plant; flowers not persistent.

*Flower longevity, sterile flowers.*—Flowers last about four months on the plant; flowers persistent.

*Quantity of flowers.*—Freely flowering; about 532 fertile flowers and about 2084 sterile flowers per panicle.

*Panicle height.*—About 19 cm.

*Panicle diameter.*—About 28 cm.

*Flower diameter, fertile flowers.*—About 4 mm.

*Flower depth (height), fertile flowers.*—About 5 mm.

*Flower diameter, sterile flowers.*—About 2.2 cm.

*Flower depth (height), sterile flowers.*—About 2 cm.

*Flower buds, fertile and sterile flowers.*—Length: About 1 mm. Diameter: About 1 mm. Shape: Ovoid. Color: Close to 144C.

*Petals, fertile flowers only.*—Arrangement: Five in a single whorl. Length: About 1 mm. Width: About 0.5 mm. Shape: Lanceolate. Apex: Acute. Base: Attenuate. Margin: Entire. Texture, upper and lower surfaces: Smooth, glabrous. Color: When opening, upper and lower surfaces: Close to 155D. Fully opened, upper and lower surfaces: Close to 155A.

*Sepals, fertile flowers.*—Quantity per flower: Three to four in a single whorl. Length: About 1.1 cm. Width: About 1.1 cm. Shape: Broadly ovate. Apex: Obtuse. Base: Obtuse. Margin: Entire. Texture, upper and lower surfaces: Smooth, glabrous. Color: When opening, upper and lower surfaces: Close to 155D. Fully opened, upper and lower surfaces: Close to 155D.

*Sepals, sterile flowers.*—Quantity per flower: Five in a single whorl. Length: Less than 0.5 mm. Width: About 0.6 mm. Shape: Oblanceolate. Apex: Acute. Base: Cuneate. Margin: Entire. Texture, upper and lower surfaces: Smooth, glabrous. Color: When opening, upper and lower surfaces: Close to 144D. Fully opened, upper and lower surfaces: Close to 144D.

*Peduncles, fertile and sterile flowers.*—Angle: Erect. Strength: Strong, sturdy. Length: About 6.5 cm. Diameter: About 4 mm. Texture: Slightly pubescent. Color: Close to 144D.

*Pedicels, fertile flowers.*—Angle: Erect to about 45° from vertical. Strength: Strong. Length: About 3 mm. Diameter: Less than 0.5 mm. Texture: Smooth, glabrous. Color: Close to 144D.

*Pedicels, sterile flowers.*—Angle: Erect to about 45° from vertical. Strength: Strong. Length: About 1.5 mm. Diameter: About 1 mm. Texture: Smooth, glabrous. Color: Close to 144D.

*Reproductive organs, fertile flowers only.*—Stamens: Quantity per flower: About ten. Anther shape: Oblong. Anther length: About 0.5 mm. Anther color: Close to 155D. Pollen amount: Moderate. Pollen color: Close to 155D. Pistils: Pistil quantity per flower: About two. Pistil length: About 2 mm. Stigma shape: Bi-lobed. Stigma color: Close to 144D. Style length: About 1 mm. Style color: Close to 144D. Ovary color: Close to 144D.

*Seeds.*—Quantity per inflorescence: Numerous. Size: Less than 0.1 mm by less than 0.1 mm. Color: Close to 200D.

Disease/pest resistance: Plants of the new *Hydrangea* have not been observed to be resistant to pests or pathogens common to *Hydrangea.*

Temperature tolerance: Plants of the new *Hydrangea* have been shown to be tolerant to temperatures ranging from about −29° C. to about 37° C.

It is claimed:

1. A new and distinct *Hydrangea* plant named 'Abetwo' as illustrated and described.

* * * * *